United States Patent [19]
Mauch

[11] Patent Number: 6,117,117
[45] Date of Patent: Sep. 12, 2000

[54] BIFURCATED CATHETER ASSEMBLY

[75] Inventor: Kevin M. Mauch, San Jose, Calif.

[73] Assignee: Advanced Cardiovascular Systems, Inc., Santa Clara, Calif.

[21] Appl. No.: 09/138,844

[22] Filed: Aug. 24, 1998

[51] Int. Cl.⁷ .................................................. A61M 25/00
[52] U.S. Cl. .......................................... 604/284; 604/103
[58] Field of Search ............................ 604/96, 101, 264, 604/53, 536, 284, 103; 606/108, 194, 195, 198; 623/1

[56] References Cited

U.S. PATENT DOCUMENTS

| | | |
|---|---|---|
| D. 376,011 | 11/1996 | Nunokawa . |
| 2,845,959 | 8/1958 | Sidebotham . |
| 2,978,787 | 4/1961 | Liebig . |
| 2,990,605 | 7/1961 | Demsyk . |
| 3,029,819 | 4/1962 | Starks . |
| 3,096,560 | 7/1963 | Liebig . |
| 3,142,067 | 7/1964 | Liebig . |
| 3,657,744 | 4/1972 | Ersek . |
| 3,908,662 | 9/1975 | Razgulov et al. . |
| 3,945,052 | 3/1976 | Liebig . |
| 4,041,931 | 8/1977 | Elliott et al. . |
| 4,047,252 | 9/1977 | Liebig et al. . |
| 4,061,134 | 12/1977 | Samuels et al. . |
| 4,108,161 | 8/1978 | Samuels et al. . |

(List continued on next page.)

FOREIGN PATENT DOCUMENTS

| | | |
|---|---|---|
| 0 461 791 A1 | 12/1991 | European Pat. Off. . |
| 0466 518 A3 | 1/1992 | European Pat. Off. . |
| 0 747 020 A2 | 2/1996 | European Pat. Off. . |
| 0 897 700 | 2/1999 | European Pat. Off. . |
| 2 740 346 | 4/1997 | France . |
| 1217402 | 3/1986 | Russian Federation . |
| 1318235 A1 | 6/1987 | Russian Federation . |
| 1389778 A2 | 4/1988 | Russian Federation . |
| 1457921 A1 | 2/1989 | Russian Federation . |
| 1482714 A2 | 5/1989 | Russian Federation . |
| WO 95/16406 | 6/1995 | WIPO . |
| WO 95/21592 | 8/1995 | WIPO . |
| WO 96/23455 | 8/1996 | WIPO . |
| WO 96/24306 | 8/1996 | WIPO . |
| WO 96/24308 | 8/1996 | WIPO . |
| WO 96/34580 | 11/1996 | WIPO . |
| WO 97/45073 | 12/1997 | WIPO . |

OTHER PUBLICATIONS

Lawrence, David D., Jr., M.D., et al., Percutaneous Endovascular Graft: Experimental Evaluation, *Radiology*, vol. 163, No. 2, pp. 357–360 (1987).

Yoshioka, Tetsuya, et a., Self–Expanding Endovascular Graft: An Experimental Study in Dogs, *Radiology*, vol. 170, pp. 1033–1037 (1989).

Parodi, J.C., M.D., et al., Transfemoral Intraluminal Graft Implantation for Abdominal Aortic Aneuyrsms, *Annals of Vascular Surgery*, vol. 5, No. 6, pp. 491–499 (1991).

Mirich, David, M.D., Percutaneously Placed Endovascular Grafts for Aortic Aneurysms: Feasibility Study, *Radiology*, vol. 170, No. 3, Part 2, pp. 1033–1037 (1989).

Chuter, Timothy A.M., BM, BS, et al., Transfemoral Endovascular Aortic Graft Placement, *Journal of Vascular Surgery*, pp. 185–196 (Aug., 1993).

U.S. Patent app. Ser. No. 08/910,857 filed Aug. 13, 1997.

*Primary Examiner*—Wynn Wood Coggins
*Assistant Examiner*—A. T. Nguyen
*Attorney, Agent, or Firm*—Fulwider Patton Lee & Utecht, LLP

[57] ABSTRACT

A bifurcated catheter assembly is provided for treating bifurcated vessels. The bifurcated catheter assembly comprises an elongate main catheter shaft having a stiffer proximal portion, a more flexible distal portion, and a pair of branch catheters attached to the distal portion. An expandable member is located on each of the branch catheters. The balloons are held together to provide a low profile as the device is advanced over the tracking guide wire. Upon reaching the bifurcated vessel, the balloons are separated and are advanced over separate guide wires into separate branches of the bifurcated vessel. The bifurcated catheter assembly can be used to dilate a stenoses or deliver and implant a Y-shaped stent in the bifurcation.

6 Claims, 5 Drawing Sheets

U.S. PATENT DOCUMENTS

| | | |
|---|---|---|
| 4,140,126 | 2/1979 | Choudhury . |
| 4,193,137 | 3/1980 | Heck . |
| 4,202,349 | 5/1980 | Jones . |
| 4,214,587 | 7/1980 | Sakura, Jr. . |
| 4,517,687 | 5/1985 | Liebig et al. . |
| 4,560,374 | 12/1985 | Hammerslag . |
| 4,562,596 | 1/1986 | Kornberg . |
| 4,577,631 | 3/1986 | Kreamer . |
| 4,617,932 | 10/1986 | Kornberg . |
| 4,652,263 | 3/1987 | Herweck et al. . |
| 4,693,249 | 9/1987 | Schenck et al. . |
| 4,728,328 | 3/1988 | Hughes et al. . |
| 4,732,152 | 3/1988 | Wallsten et al. . |
| 4,739,762 | 4/1988 | Palmaz . |
| 4,787,899 | 11/1988 | Lazarus . |
| 4,793,348 | 12/1988 | Palmaz . |
| 4,795,458 | 1/1989 | Regan . |
| 4,795,465 | 1/1989 | Marten . |
| 4,830,003 | 5/1989 | Wolff et al. . |
| 4,872,874 | 10/1989 | Taheri . |
| 4,878,906 | 11/1989 | Lindemann et al. . |
| 4,892,539 | 1/1990 | Koch . |
| 4,969,890 | 11/1990 | Sugita et al. . |
| 4,969,896 | 11/1990 | Shors . |
| 4,994,071 | 2/1991 | MacGregor . |
| 5,026,377 | 6/1991 | Burton et al. . |
| 5,047,050 | 9/1991 | Arpesani . |
| 5,104,399 | 4/1992 | Lazarus . |
| 5,108,424 | 4/1992 | Hoffman, Jr. et al. . |
| 5,127,919 | 7/1992 | Ibrahim et al. . |
| 5,156,619 | 10/1992 | Ehrenfeld . |
| 5,178,630 | 1/1993 | Schmitt . |
| 5,178,634 | 1/1993 | Ramos-Martinez . |
| 5,197,976 | 3/1993 | Herweck et al. . |
| 5,197,977 | 3/1993 | Hoffman, Jr. et al. . |
| 5,304,220 | 4/1994 | Maginot . |
| 5,316,023 | 5/1994 | Palmaz et al. . |
| 5,360,443 | 11/1994 | Barone et al. . |
| 5,443,497 | 8/1995 | Venbrux . |
| 5,443,498 | 8/1995 | Fontaine . |
| 5,456,712 | 10/1995 | Maginot . |
| 5,507,769 | 4/1996 | Marin et al. . |
| 5,522,880 | 6/1996 | Barone et al. . |
| 5,527,355 | 6/1996 | Ahn . |
| 5,562,724 | 10/1996 | Chuter . |
| 5,562,726 | 10/1996 | Chuter . |
| 5,571,167 | 11/1996 | Maginot . |
| 5,571,170 | 11/1996 | Palmaz et al. . |
| 5,571,171 | 11/1996 | Barone et al. . |
| 5,571,173 | 11/1996 | Parodi . |
| 5,575,817 | 11/1996 | Martin . |
| 5,578,071 | 11/1996 | Parodi . |
| 5,578,072 | 11/1996 | Parodi . |
| 5,591,228 | 1/1997 | Edoga . |
| 5,591,229 | 1/1997 | Parodi . |
| 5,609,627 | 3/1997 | Goiocoechea et al. . |
| 5,613,980 | 3/1997 | Chauhan ................ 604/98 X |
| 5,617,878 | 4/1997 | Taheri . |
| 5,632,763 | 5/1997 | Giastra . |
| 5,639,278 | 6/1997 | Dereume et al. . |
| 5,643,340 | 7/1997 | Nunokawa . |
| 5,669,924 | 9/1997 | Shaknovich . |
| 5,720,735 | 2/1998 | Dorros ................... 604/284 |
| 5,755,771 | 5/1998 | Penn et al. . |
| 5,827,320 | 10/1998 | Richter et al. ............ 606/194 |

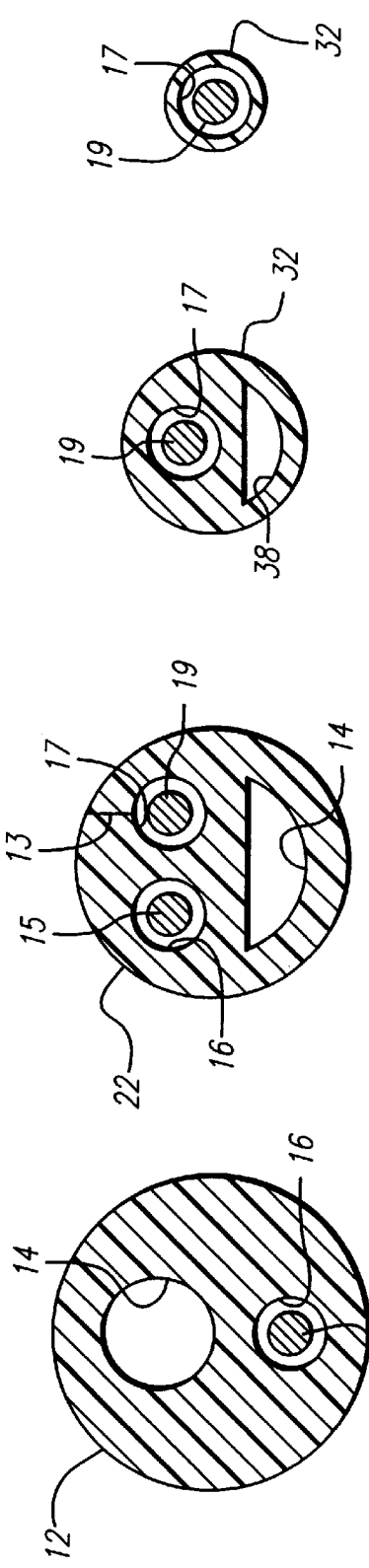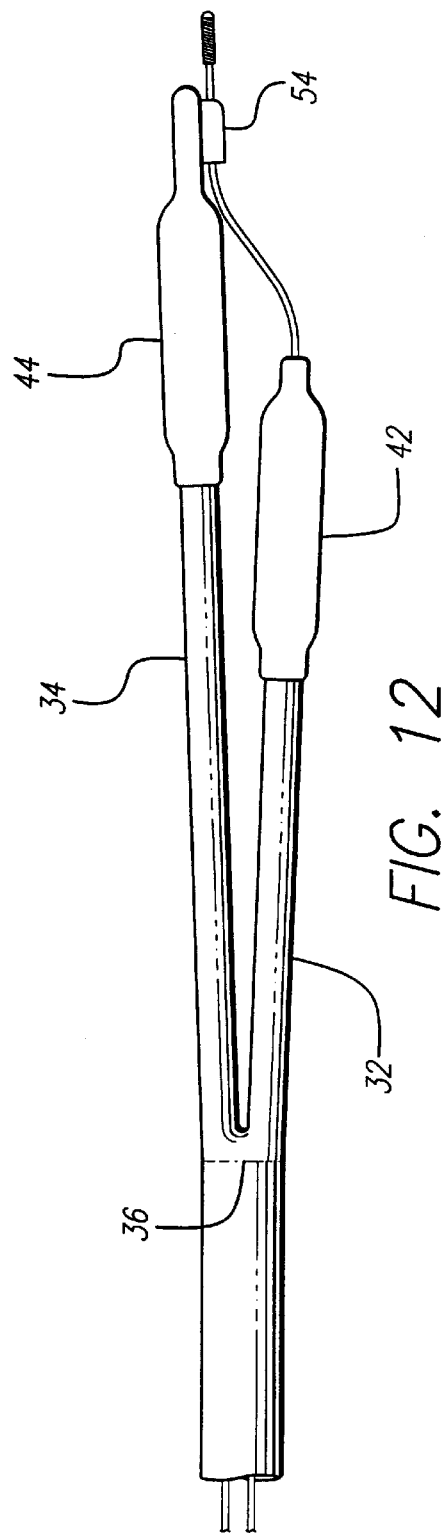

BIFURCATED CATHETER ASSEMBLY

BACKGROUND OF THE INVENTION

The present invention relates in general to balloon catheters employed in the treatment of vascular diseases. More particularly, the present invention relates to a bifurcated catheter assembly which has two dilation balloons in parallel at the distal end of a single catheter shaft. The bifurcated catheter assembly provides an improved means for treating arterial bifurcations.

In a medical procedure known as percutaneous transluminal coronary angioplasty (PTCA), a balloon catheter is used to treat a coronary artery (or other vessel) which has become narrowed or restricted due to the accumulation of plaque along the artery wall. In the PTCA procedure, a balloon catheter is inserted percutaneously and is advanced through the lumen of the coronary artery to the site of a stenosis. The balloon is then inflated to press the plaque against the artery wall thereby dilating the lumen of the artery and establishing adequate blood flow.

After the PTCA procedure has been performed, a stent (which is well known in the art) may be deployed in the treated area to prevent restenosis and maintain a clear pathway for the flow of blood. A balloon catheter with an expandable stent mounted over the balloon is advanced through the lumen until the stent is in the desired location. The balloon is then temporarily inflated thereby expanding and implanting the stent in the vessel. The balloon is then deflated and the balloon catheter assembly is removed from the lumen, leaving the implanted stent in the vessel to support the vessel wall and prevent development of restenosis.

Although most diseased arteries can be successfully treated in this manner using conventional balloon catheters and stents, arteries which are diseased at a bifurcation are difficult to treat with the devices currently available. For example, when a conventional balloon catheter is used to treat one of the vessel passages at a bifurcation during PTCA, the pressure from the expansion of the balloon in the treated passage can restrict the flow of blood to the untreated passage by pushing the carina over the ostium of the untreated vessel. In addition, the pressure of the balloon in the treated passage may shift the plaque from the treated passage to the untreated passage. If sufficient plaque is shifted to the untreated passage, the ostium of the untreated passage can becomes so occluded that it becomes difficult or impossible to insert a guide wire and catheter to perform a PTCA in the untreated vessel.

Deploying a stent at a bifurcation is also very challenging because the stent must overlay the entire diseased area of the bifurcation, yet not itself compromise blood flow. Conventional stents are designed to repair areas of blood vessels that are removed from bifurcations and, since a conventional stent generally terminates at right angles to its longitudinal axis, the use of conventional stents in the region of a vessel bifurcation may result in blocking blood flow of a side branch (commonly referred to as "jailing" the side branch) or fail to repair the bifurcation to the fullest extent necessary. To be effective, the stent must overlay the entire circumference of the ostium to a diseased portion and extend to a point within and beyond the diseased portion. Where the stent does not overlay the entire circumference of the ostium to the diseased portion, the stent fails to completely repair the bifurcated vessel.

To overcome the problems and limitations associated with the use of conventional stents, a Y-shaped stent has been proposed for the treatment of bifurcations. Such a stent has the advantage of completely repairing the vessel at the bifurcation without obstructing blood flow in other portions of the bifurcation. In addition, such a stent allows access to all portions of the bifurcated vessel should further interventional treatment be necessary. In a situation involving disease in the origin of an angulated aorta-ostial vessel, such a stent would have the advantage of completely repairing the vessel origin without protruding into the aorta or complicating repeat access. The proposed Y-shaped stent provides an improved device for repairing bifurcations, however, the delivery and deployment of such a stent cannot be easily accomplished with a conventional balloon catheter.

Because a conventional balloon catheter is not adequate for treating an arterial bifurcation, many physicians currently employ a "kissing balloons" technique in which two separate balloon catheters are inserted into a guide catheter and each balloon tracks over a separate guide wire. The guide catheter is advanced to a point proximal of the bifurcation site and two guide wires are then advanced from the distal end of the guide catheter into separate vessel passages. The two balloon catheters then track the guide wires into the respective passages. The balloons are simultaneously inflated using either separate inflation media or from a single source using a manifold which divides the flow. The two catheters are used together for PTCA or stenting so that both vessel passages at a bifurcation site can be treated simultaneously.

Although generally effective, the use of two single balloon catheters to treat arterial bifurcations has significant drawbacks. For example, the presence of two similar catheters exiting the proximal end of the guide catheter makes it difficult for a physician to manage both devices without becoming confused as to which catheter controls which balloon. Furthermore, the presence of two balloon catheters within one guide catheter creates a large device profile thereby limiting the amount of radiopaque dye which can be injected into the vessel to allow the physician to view the bifurcation.

Efforts have been made to develop a balloon catheter which is designed specifically for the treatment of arterial bifurcations. Such efforts have led to the proposal of a Y-shaped balloon disposed at the distal end of a catheter which is inflated in a bifurcation to treat both passages simultaneously. Although a Y-shaped balloon would provide an improvement over the use of two separate balloon catheters, the proposed device may not be practical due to challenges of manufacturing a Y-shaped balloon, attaching it to a catheter shaft, and properly positioning it at a bifurcated blood vessel. A device of this type is described in the international patent application WO 97/16217 dated Oct. 30, 1995 and entitled Angioplasty Device for Arterial Bifurcation.

Thus, there exists a need for an improved balloon catheter which can be used to effectively treat arterial bifurcations both for PTCA and stent delivery and deployment. It is also desirable that such a balloon catheter be easy to use, inexpensive to manufacture, and constructed from materials which are common in the industry today. The present invention addresses this need.

SUMMARY OF THE INVENTION

The present invention provides a bifuircated catheter assembly which can be used to simultaneously dilate stenoses in both the main and the side branch vessels of a bifurcation and also provides a means to quickly and easily deliver and deploy a Y-shaped stent. The invention comprises a single catheter shaft having two individual parallel balloons at the distal end. The parallel balloons track separate guide wires into separate blood vessel passages at a bifurcation and are inflated simultaneously by inflation media from a common source. The present invention is designed primarily for use in coronary arteries, however, it may also be used to treat other vessels such as the renals, abdominal aorta, femoral, and carotid arteries.

The bifurcated catheter assembly of the present invention includes a main catheter body with three lumens in its distal portion. The first lumen is an inflation lumen for pressurized inflation media which is used to inflate and deflate the balloons. The second lumen is a guide wire lumen which contains the tracking guide wire and the third lumen is also a guide wire lumen which contains an integrated guide wire.

Two parallel catheter branches are connected to the distal end of the main catheter body. Each of the parallel catheter branches has two lumens. One lumen is an inflation lumen which communicates with the inflation lumen in the main catheter body and the other lumen is a guide wire lumen in communication with one of the guide wire lumens in the main catheter body. An expandable member such as a balloon is located on the periphery of each catheter branch which is in communication with the inflation lumen in each catheter branch. An inflation notch on the side of each catheter branch allows pressurized inflation media to enter and exit the balloons. The guide wire lumen in each catheter branch extends all the way to the distal end allowing the guide wires to exit distally from the respective branches.

The tracking guide wire is advanced through the main vessel and the integrated guide wire is advanced through the ostium and into the side branch vessel at the bifurcation. With one guide wire advanced into each passage of the bifurcation, the bifurcated catheter assembly is advanced so that the first balloon tracks the tracking guide wire into the main vessel passage and the second balloon tracks the integrated guide wire into the side-branch vessel passage.

The bifurcated catheter assembly can be used at an arterial bifurcation both for PTCA and for stent delivery and implanting. Other features and advantages of the present invention will become apparent from the following detailed description, taken in conjunction with the accompanying drawings, which illustrate, by way of example, the features of the invention.

BRIEF DESCRIPTION OF THE DRAWINGS

FIG. 6 is a cross-sectional view in enlarged scale taken along the line 6—6 in FIG. 5 of the proximal portion of the main catheter body.

FIG. 7 is a cross-sectional view in enlarged scale taken along the line 7—7 in FIG. 5 of the distal portion of the main catheter body.

FIG. 8 is a cross-sectional view in enlarged scale taken along the line 8—8 in FIG. 5 of the proximal portion of one of the catheter branches.

FIG. 9 is a cross-sectional view in enlarged scale taken along the line 9—9 in FIG. 5 of the distal portion of one of the catheter branches.

FIG. 12 is an elevational view of the bifurcated catheter assembly showing the catheter branches coupled together.

DETAILED DESCRIPTION OF THE PREFERRED EMBODIMENTS

Figure 1:
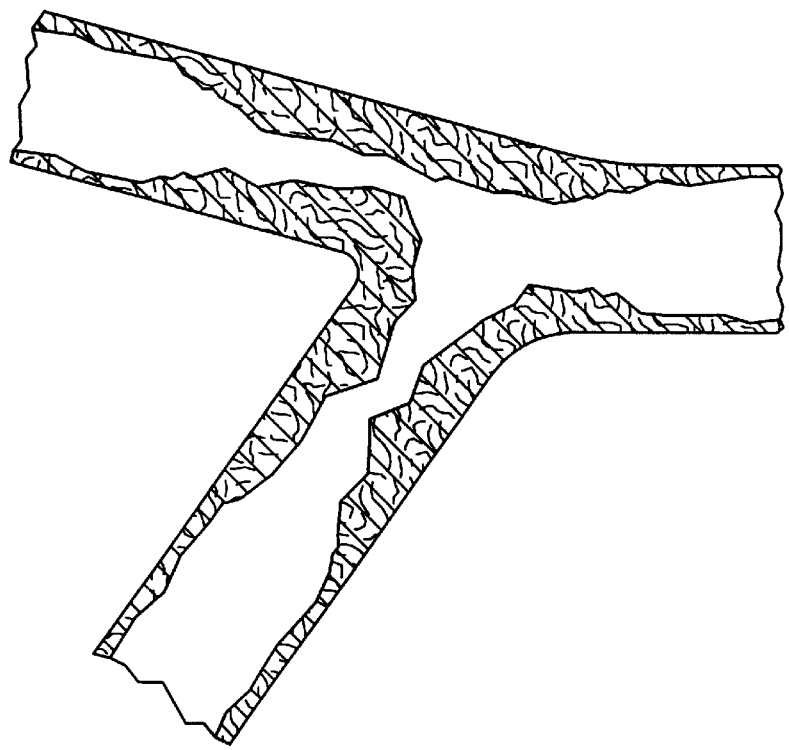
FIG. 1 is a sectional view of a diseased arterial bifurcation.

The present invention includes an assembly and method for treating bifurcations in the coronary arteries, veins, arteries and other vessels in the body. As shown in FIG. 1, an arterial bifurcation is a site within the vasculature of a body where an artery divides into two vessel passages. FIG. 1 also illustrates how plaque can build up on the artery walls creating a narrowing known as a stenosis. The stenosis can be dilated using a balloon catheter to compress the plaque against the vessel wall in a procedure known as PTCA. After the PTCA procedure, a stent is deployed in the vessel to reduce the likelihood of the development of restenosis.

Figure 2:
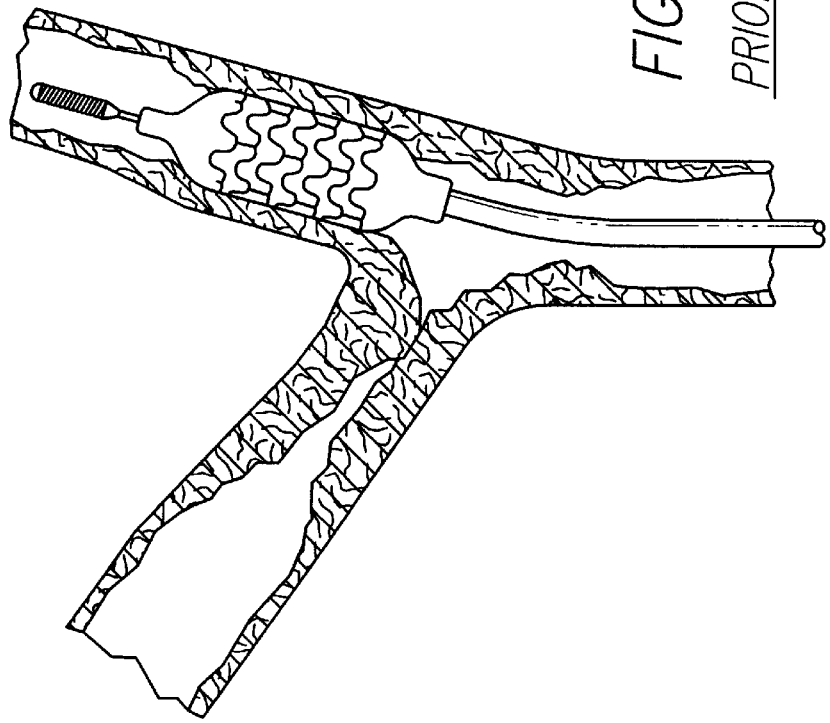
FIG. 2 is a sectional view of an arterial bifurcation showing a prior art single balloon catheter used to dilate the main vessel.
Figure 4:
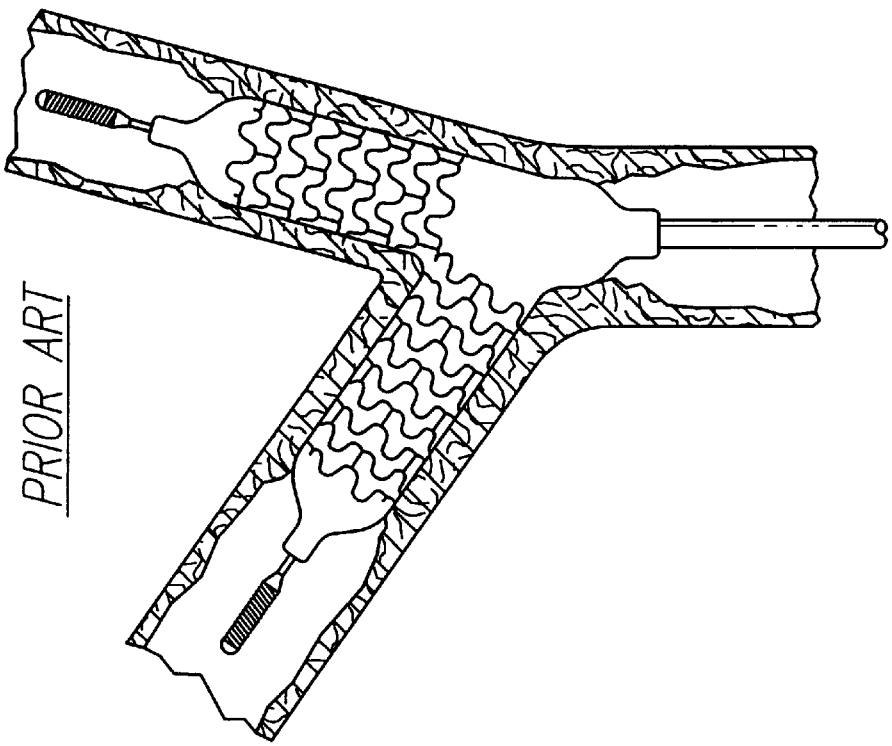
FIG. 4 is an sectional view of an arterial bifurcation showing a prior art Y-shaped balloon used to dilate both the main and side branch vessels.
Figure 3:
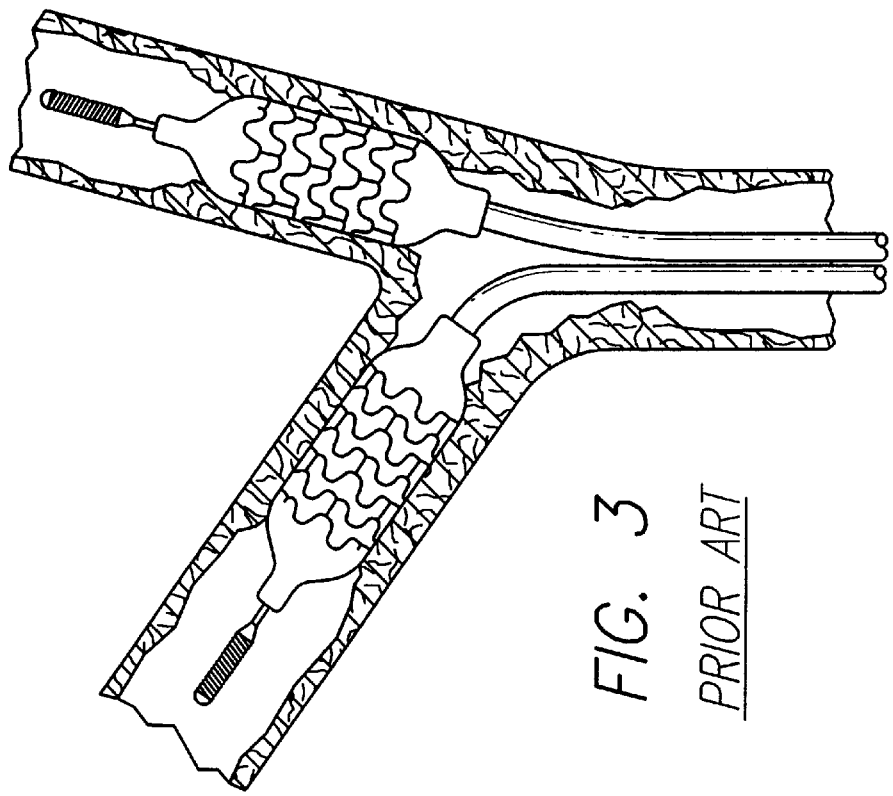
FIG. 3 is an sectional view of an arterial bifurcation showing two prior art balloon catheters used to simultaneously dilate both the main and side branch vessels.

Prior art techniques for treating arterial bifurcations have proved less than satisfactory. For example, FIGS. 2–4 depict prior art techniques for treating arterial bifurcations which include using a single balloon, two single balloons and a Y-shaped balloon. Referring to FIG. 2, a single balloon catheter is inserted into one branch of a bifurcation and is inflated to dilate the stenosis. Using a single balloon catheter to treat an arterial bifurcation requires dilating each vessel passage of the bifurcation individually. Using this approach, the dilation of the treated passage may push against the wall of the untreated passage thereby impeding the blood flow to the untreated branch and also may shift plaque from the treated passage to the untreated passage. Therefore, this technique is inadequate and often produces undesirable results which can harm the patient.

Many physicians attempt to treat a bifurcation by employing a "kissing balloon" technique. Referring to FIG. 3, this prior art device and method uses two separate balloon catheters which are both inserted into a guide catheter and track separate guide wires. One balloon is advanced into each of the vessel passages at the bifurcation site and the balloons are simultaneously inflated to dilate a stenosis or to deliver and deploy two separate stents to the bifurcation site after the vessels have been dilated. In practice, however, the use of two separate single balloon catheters is cumbersome and it can be difficult for a physician to manage both devices. In addition, the flow of contrast through the guide catheter is restricted by the presence of two catheter shafts within the guide catheter lumen thereby making it difficult for the physician to view the area being treated.

As illustrated in FIG. 4, another prior art device includes a single catheter with a Y-shaped balloon at the distal end and has been proposed as an improved means for treating arterial bifurcations. The prior art discloses a Y-shaped balloon being advanced through the lumen of a vessel and inflated at a bifurcation to dilate both passages simultaneously or to implant a Y-shaped stent. Although the Y-shaped balloon would provide an improvement over the kissing balloons technique, the practicality of the proposed Y-shaped balloon is doubtful because it presents manufacturing challenges, problems associated with positioning (e.g. wire wrapping) and deployment at the bifurcation, and higher profiles.

All of the prior art methods for treating an arterial bifurcation depicted in FIGS. 2–4 have various drawbacks which have been solved by the present invention.

Referring to FIGS. 5–10 and 12, the bifurcated catheter assembly of the present invention provides two separate balloons in parallel which can be advanced into separate passages of an arterial bifurcation and inflated simultaneously to dilate stenoses or to deploy a stent. The bifurcated catheter assembly 10 includes, generally, main catheter body 11 with a proximal portion 12 having first inflation lumen 14 and first guide wire lumen 16 extending therethrough. The proximal portion of the main catheter body preferably is a stainless steel tube surrounded by a polymer jacket (not shown) which can be formed of various materials to increase lubricity including polyethylene, nylon, polyethyl ether ketone, and copolyester-elastomer. An inflation hub 21 is located at the proximal end of the proximal portion of the main catheter body for attaching an inflation device.

Figure 5:
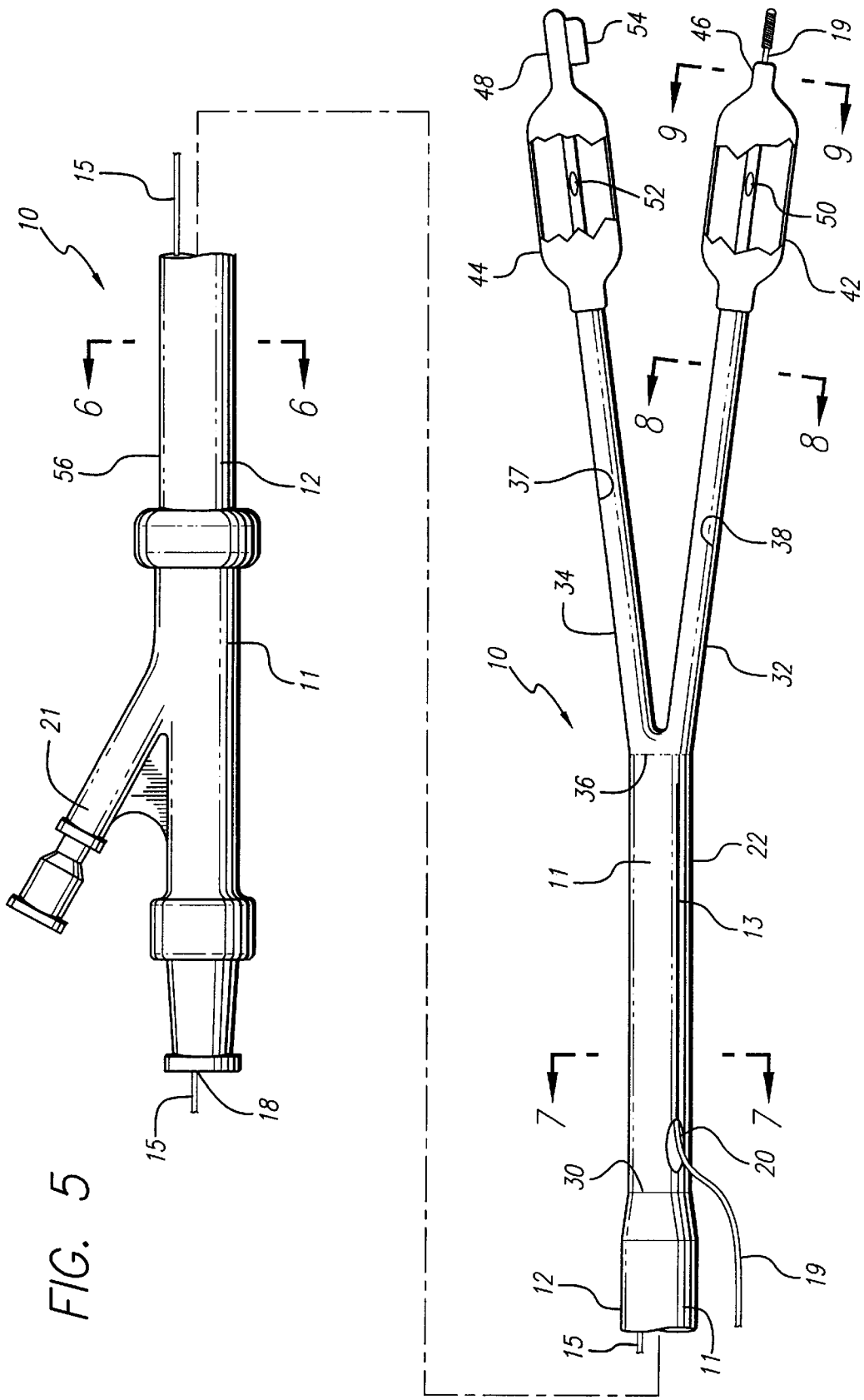
FIG. 5 is a side elevational view of a bifurcated dilation catheter embodying the present invention.

In the preferred embodiment, the bifurcated catheter assembly is of the rapid exchange type, which is known in the art. Referring to FIGS. 5 and 6, first guide wire lumen 16 includes first exit port 18 which is at the proximal end of catheter assembly 10. Integrated guide wire 15 slidably extends from outside first exit port 18 and into and through first guide wire lumen 16. As depicted in FIG. 7, second guide wire lumen 17 is of the rapid exchange type and is configured to slidably receive tracking guide wire 19. The second guide wire lumen exits catheter body 11 at second exit port 20.

Optionally, slit 13 could be provided in catheter body 22 between guide wire exit port 20 and a location just proximal of balloon 42. This would allow the catheter body to be "peeled away" from the tracking guide wire 19 to allow for more convenient catheter exchange.

The proximal portion 12 of main catheter body 11 is connected to distal portion 22 of main catheter body 11. The distal portion of the main catheter body preferably is formed from a polymer material to provide increased flexibility in the distal portion of the catheter. The distal portion of the main catheter body includes an extension of first inflation lumen 14 for carrying inflation media, first guide wire lumen 16 containing integrated guide wire 15 and second guide wire lumen 17 containing tracking guide wire 19. The connection 30 between the proximal portion and the distal portion of the main catheter body allows for the continuous flow of inflation media between the proximal and distal portions with no leaks.

A cross-section through catheter branch 32 appears as FIG. 8. Catheter branch 34 has a similar cross-sectional configuration.

The distal portion 22 of main catheter body 11 is connected to first and second parallel catheter branches 32 and 34, respectively. The connection 36 between the distal portion of the main catheter body and each of the parallel catheter branches allows for continuous flow of inflation media from the first inflation lumen in the distal shaft to second and third inflation lumens 37,38 in each of the catheter branches. The parallel catheter branches 32,34 respectively contain second and third inflation lumens 37,38 for communicating inflation media and first and second guide wire lumens 16,17 for carrying the integrated 15 and tracking guide wires 19. The first and second catheter branches have distal tips 46,48, respectively, through which the guide wires exit the guide wire lumens. The tracking guide wire 19 exits from distal tip 46 of first catheter branch 32 and integrated guide wire 15 exits from distal tip 48 of second catheter branch 34. As shown in FIG. 12, attached to the side of the distal end of second catheter branch 34 is a coupling device 54 in the form of a short tube. During advancement of the catheter assembly, the tracking guide wire 19 exits the first catheter branch 32 and is threaded through the coupling device in the second catheter branch 34 to hold the two catheter branches together.

Mounted on catheter branches 32,34, are respective expandable members preferably in the form of balloons 42,44. The balloons can be formed of many different materials including polyethylene, polyolefin copolymer, polyethylene teraphthalate, nylon, and PeBax. Inflation hub 21 receives pressurized inflation fluid and supplies the inflation fluid to inflation lumens 14, 37 and 38. Each catheter branch includes inflation notch 50,52, respectively, which allows inflation media to exit the catheter and inflate the expandable members.

In the preferred embodiment, the overall catheter is about 135 cm to 150 cm long, and the main catheter body between inflation hub 21 and connection 30 is about 125 cm in length. The proximal portion of the main catheter body preferably has a diameter of about 0.75 mm and the distal portion of the main catheter body between connection 30 and 36 has a diameter of about 1.5 mm. The first catheter branch 32 preferably is about 10 cm in length with a diameter of about 1 mm and the second catheter branch 34 is about 12 cm in length with a diameter of about 1 mm. Typically, the expandable members are balloons which are preferably from about 1.5 mm to about 4.5 mm in diameter when expanded and are about 20 mm in length, for treating coronary arteries. The foregoing dimensions will vary greatly depending upon the particular application and body lumen being treated.

The assembly of the present invention is configured for low profile delivery without compromising pushability and trackability over both guide wires. The proximal portion 12 of main catheter shaft 11 may be made by necking the jacket material over the stainless steel tubing. The jacketed tube is then connected to the distal portion 22 of the main catheter shaft. Mandrels are inserted into the guide wire lumens 16, 17 and inflation lumens to prevent the lumens from collapsing during the fusing phase when heat is applied and the proximal portion is heat fused to the distal portion of the main catheter shaft. After junction 30 has cooled, the mandrels are removed leaving continuous and leak-proof inflation lumens which extend all the way through the catheter assembly shaft.

Each of parallel catheter branches 32 and 34 is constructed as is standard in the art of catheter assembly. Balloons 42 and 44 are attached to each of the branches using a known technique such as heat seal, adhesive, laser weld, or solvent bond or the balloons are formed as one piece out the same tubing material as catheter branches. The two parallel catheter branches are then connected to the distal portion of the main catheter body similarly using heat to complete the assembly. The method of assembly of the catheter may vary depending upon available materials and manufacturer preferences.

In operation, tracking guide wire 19 is inserted percutaneously into, for instance, the femoral artery and is maneuvered to the bifurcation site such that the distal end of the tracking guide wire is in the main vessel passage distal to the bifurcation. The proximal end of tracking wire 19 is inserted into the short tube of coupling device 54. The proximal end of tracking wire 19 is then inserted into distal tip 46 of catheter branch 32. Passing tracking wire 19 through the tips of both branches together. This allows for smooth, uninterrupted movement of the catheter to the target site. The bifurcated catheter assembly 10 is then advanced over the tracking guide wire such that balloons 42 and 44 are in the main vessel passage just distal to the bifurcation. Because this invention is a rapid-exchange type of catheter, a portion of the tracking guide wire 19 is located external to the catheter and therefore there is very little frictional drag during advancement of the assembly. When the balloons have been advanced distally beyond the bifurcation, the tracking guide wire 19 is withdrawn proximally until its distal end pulls out of coupling device 54 thereby decoupling the balloons from each other. Tracking wire 19 is then advanced back through tip 46 into the main vessel passage. The bifurcated catheter assembly is then withdrawn proximally along the tracking guide wire so that the balloons are proximal to the bifurcation. With the tracking guide wire still in the main vessel passage, the integrated guide wire, which has been contained within second guide wire lumen 17, is advanced from the distal tip of the other catheter branch 34 into the side-branch vessel. At this point, there is one guide wire exiting the distal tip of each catheter branch and entering a separate passage of the bifurcation whereby the tracking guide wire is in the main vessel passage and the integrated guide wire is in the side branch vessel passage. The catheter assembly is then advanced over the guide wires whereby each balloon tracks a guide wire into a separate passage of the bifurcation until the balloons are positioned at the stenosed areas.

Figure 10:
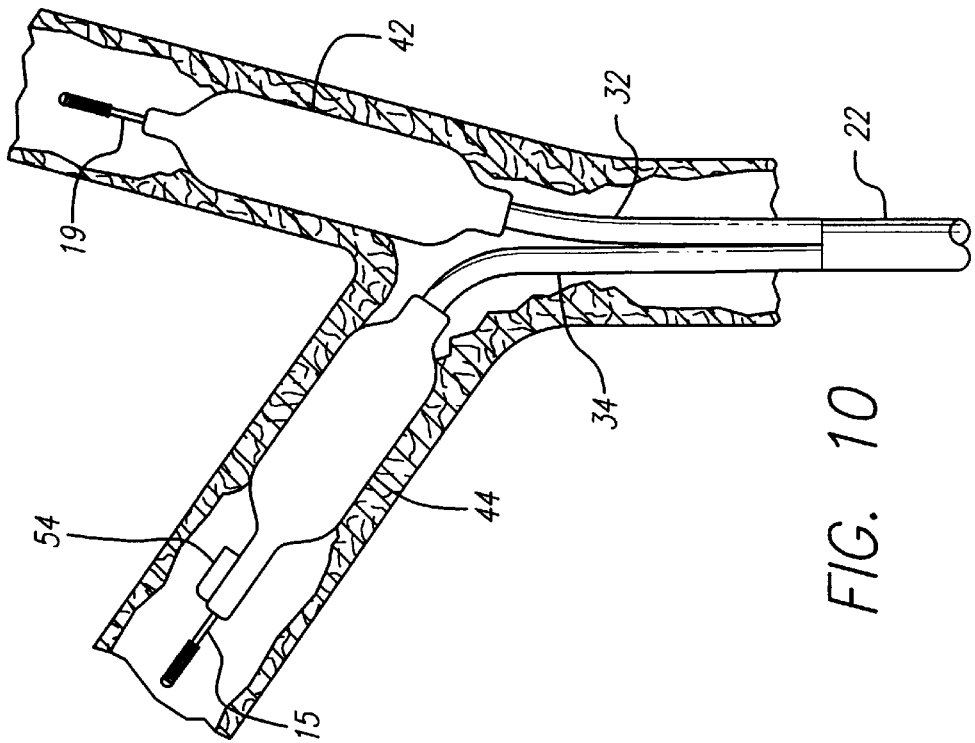
FIG. 10 is a sectional view of an arterial bifurcation showing both balloons dilated during PTCA.

An inflation syringe (or pump) located outside the patient's body is attached to inflation hub 21 and supplies pressurized inflation media through the inflation lumens and into balloons 42 and 44. With one balloon in each passage, the balloons can be simultaneously inflated to dilate a stenosis during a PTCA procedure as illustrated in FIG. 10. Because both passages of the bifurcation are treated simultaneously, neither of the passages is pinched off or damaged by the procedure. In addition, all the plaque in the bifurcation is compressed at the same time and therefore there is no shifting of plaque from one passage to the other. After the stenosed areas have been dilated, the balloons are deflated to their minimum dimensions so that they can be easily withdrawn from the vessels.

In the preferred embodiment shown in the figures, the device could be removed together-with integrated wire 17, while tracking wire 19 remains in the main vessel passage. This is facilitated by the rapid exchange configuration of the device, wherein tracking wire 19 exits catheter body 22 through exit port 20, which is located about 25 cm proximal from the distal end of the balloon.

The slitted configuration mentioned above would further facilitate a rapid exchange procedure. Optionally, lumen 16 through which integrated wire 17 passes, could be provided with a rapid exchange guide wire exit port on the catheter body. This would allow the maintenance of each wire in position in their respective vessels during catheter exchange. As a further option, lumen 16 could also be slitted to further facilitate rapid exchange. In this case a second guide wire exit port would be provided distal of the proximal hub.

Figure 11:
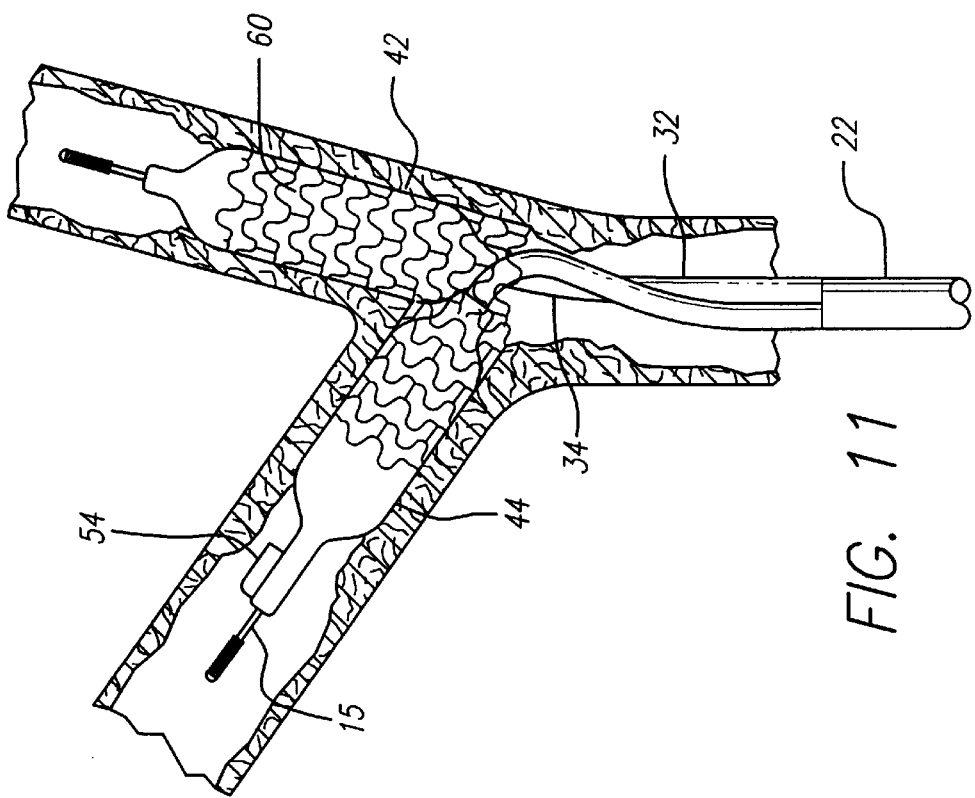
FIG. 11 is a sectional view of an arterial bifurcation showing the invention deploying a stent.

Another advantage of the invention is the ability to deliver and implant a Y-shaped stent to the bifurcation as shown in FIG. 11. In this procedure, the bifurcated catheter assembly 10 has Y-shaped stent 60 mounted on the balloons. The balloons 42 and 44 are held together during delivery to provide a low profile allowing room for radiopaque dye to be injected into the bloodstream during the procedure. The tracking guide wire is advanced into the main vessel to a point distal of the bifurcation. The bifurcated catheter assembly is then advanced over the tracking guide wire so that the stent is distal to the bifurcation. The tracking guide wire is then withdrawn proximally thereby decoupling the balloons. The catheter assembly is then withdrawn proximally until it is proximal to the bifurcation with the tracking guide wire remaining in the main vessel. The integrated guide wire is then advanced out of branch catheter 34 and into the side-branch vessel. The catheter assembly is advanced over both guide wires until the balloons and stent are anchored in the bifurcation. The balloons are inflated and the stent expanded and implanted in the bifurcation.

From the foregoing, it will be appreciated that the bifurcated catheter assembly of the invention allows both passages of a diseased bifurcation to be dilated simultaneously during a PTCA procedure, thereby avoiding any possible damage to the vessels and avoiding the transfer of plaque from one passage to the other. The bifurcated catheter assembly also facilitates the delivery and deployment of a Y-shaped stent which is designed specifically for use in a bifurcation. The invention is made of materials commonly used in the industry today and is simple to use and easy to manufacture.

While a particular form of the invention has been illustrated and described, it will be apparent that various modifications can be made without departing from the spirit and scope of the invention.

What is claimed is:

1. A bifurcated catheter assembly for treating bifuircated vessels, comprising:

an elongate main catheter body having a proximal portion and a distal portion, a first inflation lumen, a first guide wire lumen, and a second guide wire lumen;

a first catheter branch connected to said distal portion of said main catheter body and having a second inflation lumen in fluid communication with said first inflation lumen in said main catheter body and said first guide wire lumen extending therethrough and in communication with said first guide wire lumen in said main catheter body;

a second catheter branch connected to said distal portion of said main catheter body and having a third inflation lumen in fluid communication with said first inflation lumen and said second guide wire lumen extending therethrough and in communication with said second guide wire lumen in said main catheter body;

a first expandable member associated with said first catheter branch and in fluid communication with said second inflation lumen;

a second expandable member associated with said second catheter branch in fluid communication with said third inflation lumen; and a coupler mounted on distal end of said first catheter branch for coupling to a distal end of said second catheter branch;

whereby said first expandable member and said second expandable member are positioned across a stenosis in a main vessel and in a side branch vessel respectively so that said expandable members can be simultaneously inflated to dilate the stenosis and restore patency to the main vessel and side branch vessel.

2. The bifurcated catheter assembly as set forth in claim 1, wherein said first and second expandable members are balloons.

3. The bifurcated catheter assembly as set forth in claim 1, wherein said first, second and third inflation lumens communicate pressurized fluid to said first and second expandable members.

4. The bifurcated catheter assembly as set forth in claim 1, wherein said coupler comprises a short tube for receiving a guidewire advanced out of said second guide wire lumen.

5. The bifurcated catheter assembly as set forth in claim 1, wherein said bifurcated catheter assembly includes an integrated guide w ire slidably received in said first guide wire lumen and a tracking guide wire slidably received in said second guide wire lumen.

6. The bifuircated catheter assembly as set forth in claim 1, wherein said first and second branches are non-movably connected to said main catheter body.

\* \* \* \* \*